United States Patent [19]

Sirrenberg et al.

[11] Patent Number: 4,533,676
[45] Date of Patent: Aug. 6, 1985

[54] 2,5-DIHALOGENOBENZOYL-(THIO)UREA INSECTICIDES

[75] Inventors: Wilhelm Sirrenberg, Sprockhoevel; Erich Klauke, Odenthal; Ingeborg Hammann, Muelheim, all of Fed. Rep. of Germany

[73] Assignee: Bayer Aktiengesellschaft, Leverkusen, Fed. Rep. of Germany

[21] Appl. No.: 487,799

[22] Filed: Apr. 22, 1983

[30] Foreign Application Priority Data

May 11, 1982 [DE] Fed. Rep. of Germany ....... 3217620

[51] Int. Cl.$^3$ .......................... A01N 9/12; A01N 9/20; C07C 127/22
[52] U.S. Cl. ............................... 514/535; 260/456 A; 260/465 D; 514/450; 514/456; 514/466; 514/522; 514/584; 514/594; 549/350; 549/362; 549/365; 549/439; 560/17; 560/34; 564/23; 564/44
[58] Field of Search ..................... 564/44, 23; 424/322, 424/304, 278, 282, 303, 309; 560/34, 17; 260/465 D, 456 A; 549/350, 362, 365, 439

[56] References Cited

U.S. PATENT DOCUMENTS

| 3,933,908 | 1/1976 | Wellinga et al. |
| 4,139,636 | 2/1979 | Sirrenberg et al. |
| 4,339,460 | 7/1982 | Ehrenfreund ..................... 564/44 X |
| 4,348,412 | 9/1982 | Ehrenfreund ..................... 564/44 X |

FOREIGN PATENT DOCUMENTS

| 0008435 | 3/1980 | European Pat. Off. |
| 0008768 | 3/1980 | European Pat. Off. |
| 57888 | 8/1982 | European Pat. Off. ............. 564/44 |
| 2123236 | 12/1971 | Fed. Rep. of Germany. |
| 2601780 | 7/1977 | Fed. Rep. of Germany. |
| 2801316 | 7/1979 | Fed. Rep. of Germany. |
| 3217619 | 11/1983 | Fed. Rep. of Germany ........ 564/44 |

Primary Examiner—Thomas A. Waltz
Attorney, Agent, or Firm—Sprung Horn Kramer & Woods

[57] ABSTRACT

A 2,5-dihalogenobenzoyl-(thio)urea of the formula

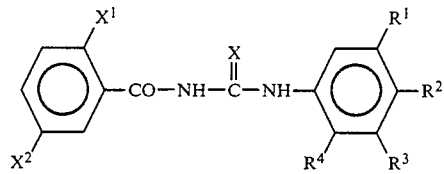

in which
X represents sulphur or oxygen,
$X^1$ and $X^2$ are identical or different and represent fluorine, chlorine, bromine or iodine,
$R^1$ represents hydrogen, halogen, or optionally substituted radicals from the series comprising alkyl, alkoxy and alkylthio,
$R^2$ represents hydrogen, halogen, cyano, nitro or optionally substituted radicals from the series comprising alkyl, alkylthio, alkylsulphonyl, alkoxy, aryloxy, alkylcarbonyl, alkoxycarbonyl, alkoxycarbonylalkyl and alkoxycarbonylalkylthio,
$R^1$ and $R^2$ together represent an optionally substituted alkylenedioxy radical or represent —CF$_2$—O—CF$_2$—O—,
$R^3$ represents hydrogen, halogen, or an optionally substituted alkyl, alkoxy or aryloxy radical, and
$R^4$ represents hydrogen, halogen, or optionally substituted radicals from the series comprising alkyl, alkylthio and alkoxy, with the exception of those cases in which X represents oxygen, $X^1$ and $X^2$ represent chlorine and (a) $R^1$ represents chlorine, $R^2$ represents OCF$_2$CHFCL and $R^3$ and $R^4$ represent hydrogen, or (b) $R^1$ represents chlorine, $R^2$ represents OCF$_3$ and $R^3$ and $R^4$ represent hydrogen, or (c) $R^2$ represents OCF$_3$ and $R^1$, $R^3$ and $R^4$ represent hydrogen, which possesses insecticidal activity.

12 Claims, No Drawings

2,5-DIHALOGENOBENZOYL-(THIO)UREA INSECTICIDES

The present invention relates to new 2,5-dihalogenobenzoyl-(thio)ureas, several processes for their preparation and their use as pest-combating agents, in particular as insecticides.

It is already known that certain benzoylureas, such as, for example, 1-(2,6-dichloro-benzoyl)-3-(4-chlorophenyl)-urea and 1-(2,6-dichloro-benzoyl)-3-(3,4-dichloro-phenyl)-urea, possess insecticidal properties (see, for example, DE-AS (German Published Specification) No. 2,123,236 and the corresponding U.S. Pat. No. 3,933,908 and U.S. Pat. No. 4,139,636), and the 2- and 2,6-substituted benzylureas and -thioureas are described as being particularly insecticidally active.

The new 2,5-dihalogenobenzoyl-(thio)ureas of the formula (I)

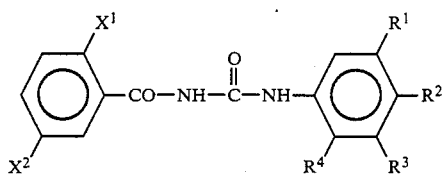

in which

X represents sulphur or oxygen, $X^1$ and $X^2$ are identical or different and represent fluorine, chlorine, bromine or iodine, $R^1$ represents hydrogen, halogen, or optionally substituted radicals from the series comprising alkyl, alkoxy and alkylthio, $R^2$ represents hydrogen, halogen, cyano, nitro or optionally substituted radicals from the series comprising alkyl, alkylthio, alkylsulphonyl, alkoxy, aryloxy, alkylcarbonyl, alkoxycarbonyl, alkoxycarbonylalkyl or alkoxycarbonylalkylthio, $R^1$ and $R^2$ together represent an optionally substituted alkylenedioxy radical or represent —CF$_2$—O—CF$_2$—O—, $R^3$ represents hydrogen, halogen, or an optionally substituted alkyl, alkoxy or aryloxy radical, and $R^4$ represents hydrogen, halogen, or optionally substituted radicals from the series comprising alkyl, alkylthio or alkoxy, with the exception of those cases in which X represents oxygen, $X^1$ and $X^2$ represent chlorine and (a) $R^1$ represents chlorine, $R^2$ represents OCF$_2$CHFCl and $R^3$ and $R^4$ represent hydrogen, or (b) $R^1$ represents chlorine, $R^2$ represents OCF$_3$ and $R^3$ and $R^4$ represent hydrogen, or (c) $R^2$ represents OCF$_3$ and $R^1$, $R^3$ and $R^4$ represent hydrogen, have been found.

These new compounds have powerful biological, in particular insecticidal, properties, which make it possible to use them as pest-combating agents, in particular as insecticides.

Furthermore, it has been found that the new 2,5-dihalogenobenzoyl-ureas of the formula (I) are obtained by a process in which (a) substituted anilines of the formula (II)

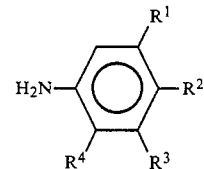

in which $R^1$, $R^2$, $R^3$ and $R^4$ have the meanings given above, are reacted with benzoyl iso(thio)cyanates of the formula (III)

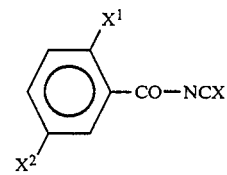

in which X, $X^1$ and $X^2$ have the meanings given above, if appropriate in the presence of a diluent, or (b) substituted phenyl iso(thio)cyanates of the formula (IV)

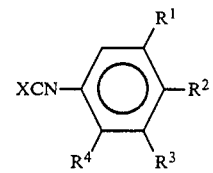

in which $R^1$, $R^2$, $R^3$, $R^4$ and X have the meanings given above, are reacted with benzoic acid amides of the formula (V)

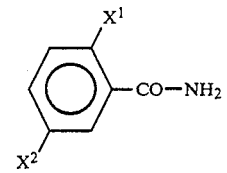

in which $X^1$ and $X^2$ have the meanings given above, if appropriate in the presence of a catalyst and, if appropriate, in the presence of a diluent.

Optionally substituted alkyl $R^1$, $R^2$, $R^3$ and $R^4$ represent straight-chain or branched alkyl having 1 to 12, preferably 1 to 6, in particular 1 to 4, carbon atoms. Optionally substituted methyl, ethyl, n- and i-propyl, n-, i-, sec- and tert.butyl may be mentioned as examples.

Optionally substituted alkoxy $R^1$, $R^2$, $R^3$ and $R^4$ represent straight-chain or branched alkoxy having preferably 1 to 6, in particular 1 to 4, carbon atoms. Optionally substituted methoxy, ethoxy, n- and i-propoxy and n-, i-, sec- and tert.butoxy may be mentioned as examples.

Optionally substituted alkylthio $R^1$, $R^2$ and $R^4$, and alkylsulphonyl $R^2$, represent straight-chain or branched alkylthio or alkylsulphonyl having preferably 1 to 6, in particular 1 to 4, carbon atoms. Optionally substituted methylthio, ethylthio, n- and i-propylthio, n-, i-, sec- and tert.-butylthio, methylsulphonyl, ethylsulphonyl, n- and i-propylsulphonyl, n-, i-, sec- and tert.butyl-sulphonyl may be mentioned as examples.

Optionally substituted aryloxy $R^2$ and $R^3$ preferably contain 6 or 10 carbon atoms in the aryl part, and phenoxy and naphthyloxy, preferably phenoxy, may be mentioned.

Optionally substituted alkylcarbonyl, alkoxycarbonyl, alkoxycarbonylalkyl or alkoxycarbonylalkylthio $R^2$ corresponds in its alkyl part to the alkyl radical $R^2$, in its alkoxy part to the alkoxy radical $R^2$ and in its alkylthio part to the alkylthio radical $R^2$.

Optionally substituted alkylenedioxy in the definition of $R^1$ and $R^2$ contains preferably 1 to 3, in particular 1 or 2, carbon atoms.

Halogen denotes (where not stated otherwise) fluorine, chlorine, bromine and iodine, preferably fluorine, chlorine and bromine.

The radicals $R^1$, $R^2$, $R^3$ and $R^4$ can be monosubstituted or polysubstituted by identical or different substituents.

Preferred substituents in this case are: halogen, the halogen atoms being identical or different and being preferably fluorine, chlorine or bromine, in particular fluorine and bromine; cyano, nitro, phenyl, alkyl, alkoxy, alkylthio, alkylthioalkyl and alkylsulphonyloxy having preferably 1 to 4 carbon atoms, halogenoalkyl, halogenoalkoxy and/or halogenoalkylthio having preferably 1 to 2 carbon atoms and preferably 1 to 5, in particular 1 to 3, halogen atoms, the halogen atoms being identical or different and being preferably fluorine, chlorine or bromine, in particular fluorine, such as trifluoromethyl, trifluoromethoxy or trifluoromethylthio; and alkoxycarbonyl having 1 to 6 carbon atoms in the alkyl part.

X preferably represents oxygen.

$X^1$ preferably represents chlorine and $X^2$ preferably represents fluorine.

The new compounds of the formula (I) possess properties which make it possible to use them as pest-combating agents; in particular, they are distinguished by an outstanding insecticidal activity.

The invention preferably relates to new compounds of the formula (I) in which

X represents sulphur or oxygen, $X^1$ and $X^2$ are identical or different and represent fluorine, chlorine or bromine, $X^1$ preferably representing chlorine and $X^2$ preferably representing fluorine, $R^1$ represents hydrogen, halogen, or an optionally halogen-substituted radical from the series comprising $C_1$-$C_6$-alkyl, $C_1$-$C_6$-alkoxy and $C_1$-$C_6$-alkylthio, $R^2$ represents hydrogen, cyano, nitro, halogen, or an optionally halogen-substituted radical from the series comprising $C_1$-$C_6$-alkyl, $C_1$-$C_6$-alkylthio, $C_1$-$C_6$-alkylsulphonyl, $C_1$-$C_6$-alkoxy, $C_1$-$C_6$-alkylcarbonyl, $C_1$-$C_6$-alkoxycarbonyl, $C_1$-$C_6$-alkoxycarbonylalkyl and $C_1$-$C_6$-alkoxycarbonylalkylthio, or represents a phenoxy which is optionally substituted by halogen, cyano, nitro, phenyl, trifluoromethyl, trifluoromethoxy, trifluoromethylthio, $C_1$-$C_6$-alkyl, $C_1$-$C_6$-alkoxy, $C_1$-$C_6$-alkylthio, $C_1$-$C_6$-alkylthioalkyl, $C_1$-$C_6$-alkylsulphonyloxy and/or $C_1$-$C_6$-alkoxycarbonyl, or $R^1$ and $R^2$ together represent alkylenedioxy which has 1 to 3 carbon atoms and is optionally substituted by fluorine and/or chlorine, or represent —$CF_2$—O—$CF_2$—O—, $R^3$ represents hydrogen, halogen, or an optionally halogen-substituted $C_1$-$C_6$-alkyl, $C_1$-$C_6$-alkoxy or phenoxy radical, and $R^4$ represents hydrogen, halogen, or optionally halogen-substituted radicals from the series comprising $C_1$-$C_6$-alkyl, $C_1$-$C_6$-alkylthio or $C_1$-$C_6$-alkoxy, with the exception of those cases in which X represents oxygen, $X^1$ and $X^2$ represent chlorine and (a) $R^1$ represents chlorine, $R^2$ represents $OCF_2CHFCl$ and $R^3$ and $R^4$ represent hydrogen, or (b) $R^1$ represents chlorine, $R^2$ represents $OCF_3$ and $R^3$ and $R^4$ represent hydrogen, or (c) $R^2$ represents $OCF_3$ and $R^1$, $R^3$ and $R^4$ represent hydrogen, halogen representing in each case fluorine, chlorine, bromine and/or iodine, preferably fluorine, chlorine and/or bromine.

Particularly preferred compounds of the formula (I) are those in which

X represents oxygen or sulphur, $X^1$ and $X^2$ are identical or different and represent fluorine, chlorine or bromine, $X^1$ preferably representing chlorine and $X^2$ preferably representing fluorine, $R^1$ represents hydrogen, fluorine, chlorine or bromine, $R^2$ represents hydrogen, chlorine, bromine, fluorine, cyano, nitro, methyl, ethyl, n-propyl, i-propyl, n-butyl- i-butyl, sec.butyl, tert.butyl, trifluoromethyl, difluoromethyl, 1,1-difluoroethyl, 1,1,2,2,2-pentafluoroethyl, trifluoromethoxy, difluoromethoxy, chlorodifluoromethoxy, 2-chloro-1,1,2-trifluoroethoxy, 1,1,2,2-tetrafluoroethoxy, 2,2-dichloro-1,1-difluoroethoxy, 1,1,2,3,3,3-hexafluoropropoxy, trifluoromethylthio, difluoromethylthio, chlorodifluoromethylthio, 2-chloro-1,1,2-trifluoroethylthio, methoxycarbonyldifluoromethylthio, 1,1,2,3,3-hexafluoropropylthio, trifluoromethylsulphonyl or methoxy-, ethoxy-, n-propoxy-, i-propoxy-, n-butoxy-, i-butoxy-, sec-butoxy- and tert.butoxycarbonyl, or represents phenoxy which is optionally substituted by halogen, nitro, cyano, $C_1$-$C_6$-halogenoalkyl or $C_1$-$C_4$-alkoxycarbonyl, or $R_1$ and $R_2$ together represent difluoromethylenedioxy or represent —$CF_2$—O—$CF_2$—O— or represent ethylenedioxy which is substituted by 3 or 4 fluorine atoms or by 3 fluorine atoms and 1 chlorine atom, $R^3$ represents hydrogen, fluorine, chlorine or bromine, and $R^4$ represents hydrogen, chlorine, bromine, trifluoromethyl, trifluoromethoxy and trifluoromethylthio, with the exception of those cases in which X represents oxygen, $X^1$ and $X^2$ represent chlorine and (a) $R^1$ represents chlorine, $R^2$ represents $OCF_2CHFCl$ and $R^3$ and $R^4$ represent hydrogen, or (b) $R^1$ represents chlorine, $R^2$ represents $OCF_3$ and $R^3$ and $R^4$ represent hydrogen, or (c) $R^2$ represents $OCF_3$ and $R^1$, $R^3$ and $R^4$ represent hydrogen.

Very particularly preferred compounds of the formula (I) are those in which $X^1$ represents chlorine, $X^2$ represents fluorine, X represents oxygen, $R^1$ represents hydrogen or chlorine, $R^2$ represents hydrogen, trifluoromethyl, trifluoromethoxy, difluoromethoxy, chlorodifluoromethoxy, chlorotrifluoroethoxy, n-pentafluoropropoxy, trifluoromethylthio, chlorodifluoromethylthio, tert.butoxycarbonyl, 4-nitrophenoxy, 4-cyanophenoxy and 4-trifluoromethylphenoxy, or $R^1$ and $R^2$ together represent chlorotrifluoroethylenedioxy or —$CF_2$—O—$CF_2$—O—,
$R^3$ represents hydrogen or chlorine, and
$R^4$ represents hydrogen.

If 3-chloro-4-trifluoro-methoxyaniline and 2-chloro-5-fluoro-benzoyl isocyanate are used as starting materials according to process variant (a), the course of the reaction can be represented by the following equation:

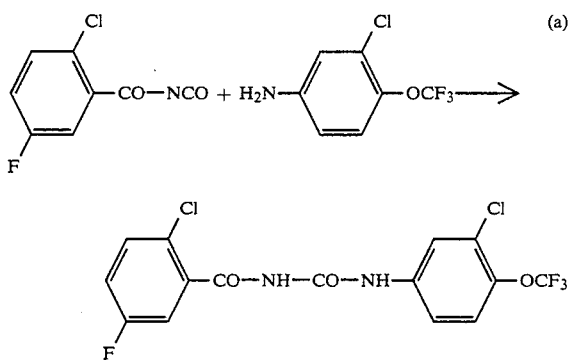

If 3-chloro-4-trifluoromethoxy-phenyl isocyanate and 2-chloro-5-fluoro-benzamide are used as starting materials according to process variant (b), the course of the reaction can be represented by the following equation:

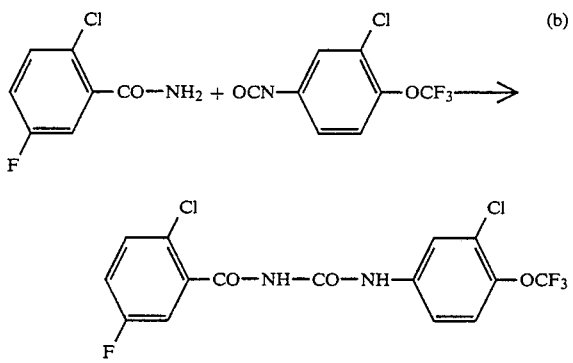

The following may be mentioned as examples of the compounds of the formula (II): 4-trifluoromethoxy-, 3,4-chlorotrifluoroethylenedioxy-, 4-trifluoromethylthio-, 3-chloro-4-chlorodifluoromethylthio-, 3-chloro-4-chlorotrifluoroethoxy-, 4-chloro-, 4-trifluoromethyl-, 3,4-dichloro-, 4-pentafluoropropoxy-, 4-methyl-, 4-ethyl-, 4-n-propyl-, 4-i-propyl-, 4-n-butyl-, 4-i-butyl-, 4-sec.butyl-, 4-tert.butyl-, 3,5-dichloro-, 4-chlorodifluoromethoxy-, 3-chloro-4-trifluoromethoxy-, 4-chlorotrifluoroethoxy, 3-chloro-4-trifluoromethylthio-, 4-bromo-, 2-bromo-, 3-chloro-4-nitrophenoxy-, 3,5-dichloro-4-(4-nitrophenoxy)-, 3,4,6-trichloro-, 2-chloro-, 3-chloro-4-trifluoromethyl-, 2-trifluoromethoxy-, 3,5-dichloro-4-(4-cyanophenoxy)-, 3,5-dichloro-4-(4-trifluoromethylphenoxy)-, 3,5-dichloro-4-(2-chloro-4-trifluoromethylphenoxy)- and 4-fluoro-aniline.

The substituted anilines of the formula (II) which are to be used as starting materials are known and can be prepared by processes and methods which are known from the literature (see, for example, DE-OS (German Published Specification) No. 2,601,780, DE-OS (German Published Specification) No. 2,801,316, DE-OS (German Published Specification) No. 2,837,524, DE-OS (German Published Specification) No. 2,843,851 and DE-OS (German Published Specification) No. 3,023,328).

The following may be mentioned as an example of the compounds of the formula (III): 2-chloro-5-fluoro-benzoyl isocyanate and -benzoyl isothiocyanate, and 2-bromo-5-fluoro-benzoyl isocyanate and -benzoyl isothiocyanate.

The starting compounds of the formula (III) are known.

The following may be mentioned as examples of the compounds of the formula (IV): 4-trifluoromethoxy-, 4-trifluoromethyl-, 4-trifluoromethylthio-, 3-chloro-4-trifluoromethoxy, 3-chloro-4-trifluoromethyl-, 3-chloro-4-trifluoromethylthio-, 3,4-chlorotrifluoroethylenedioxy-, 3-chloro-4-chlorodifluoromethylthio-, 3-chloro-4-chlorotrifluoroethoxy-, 4-chloro-, 2-chloro-, 3,4-dichloro-, 4-pentafluoropropoxy-, 4-methyl-, 4-ethyl-, 4-n-propyl-, 4-i-propyl-, 4-n-butyl-, 4-i-butyl-, 4-sec.butyl-, 4-tert.butyl-, 3,5-dichloro-, 4-chlorodifluoromethoxy-, 3-chloro-4-trifluoromethoxy-, 4-chlorotrifluoroethoxy-, 3-chloro-4-trifluoromethylthio-, 2-bromo-, 4-bromo-, 3-chloro-4-nitrophenoxy-, 3,5-dichloro-4-(4-nitrophenoxy)-, 3,4,6-trichloro-, 2-trifluoromethoxy-, 3,5-dichloro-4-(4-cyanophenoxy)-, 3,5-dichloro-4-(4-trifluoromethylphenoxy)-, 3,5-dichloro-4-(2-chloro-4-trifluoromethylphenoxy)- and 4-fluoro-phenyl iso(thio)cyanate.

Compounds of the formula IV are known and can be prepared by generally known processes and methods.

The following may be mentioned as examples of the compounds of the formula (V): 2-chloro-5-fluoro-benzoic acid amide and 2-bromo-5-fluoro-benzoic acid amide.

Compounds of the formula (V) are known and can be prepared by known methods (see, for example, J. Am. Chem. Soc. 81, 94 (1959).

Suitable diluents are virtually all inert organic solvents. These include in particular aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylacetamide and N-methylpyrrolidone, and tetramethylenesulphone.

Tertiary amines, such as triethylamine and 1,4-diazabicyclo[2,2,2]-octane, and organic tin compounds, such as, for example, dibutyl-tin dilaurate, can preferably be used as catalysts for the reaction according to process variant (b).

The reaction temperature can be varied within a relatively wide range. In general, process variant (a) is carried out at between 20° and 180° C., preferably between 60° and 120° C., and process variant (b) is carried out at between 20° and 200° C., preferably between 60° and 190° C. The process variants according to the invention are carried out in general under atmospheric pressure.

To carry out the process variants according to the invention, the starting materials are usually employed in about equimolar amounts. An excess of one or the other of the reaction components has no substantial advantages.

The reaction products are worked up by customary methods, for example by filtering off the precipitated product under suction, or by dissolving out undesired by-products from the reaction mixture. They are characterized by their melting point.

The active compounds are well tolerated by plants and are suitable for combating animal pests, especially insects, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculate.* From the order of the Thysanura, for example *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and Thrips tabaci. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., Trichoplusia ni, *Carpocapsa pomonella, Pieris* spp., *Chilo* spp., *Pyrausta nubilalis, Ephestia kuehniella, Galleria mellonella, Cacoecia podana, Capua reticulana, Choristoneura Fumiferana, Clysia ambiguella, Homona magnanima* and *Tortrix viridana,* Tineola bisseliella, *Tusea pellionella, Hofmannophila pseudospretella.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The new active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example also be used as auxiliary solvents. As liquid solvents, there are suitable in the main: strongly polar solvents, such as dimethylformamide and dimethylsulphoxide; by liquefied gaseous extenders or carriers are meant liquids which are gaseous at normal temperature and under normal pressure, for example aerosol propellant, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents there are suitable: for example lignin-sulphite waste liquors and methylcellulose.

Compounds which correspond to the formula I and have aniline radicals such as those contained in the compounds which were described in DE-AS (German Published Specification) Nos. 1,123,236 and 3,041,957; European Patent Specification Nos. 6,184, 7,687, 8,768, 13,414, 14,674, 14,675, 14,676, 16,729, 23,884, 25,363, 30,518, 31,974, 33,231, 35,084, 38,776, 40,179, 44,278 and 44,410, and Japanese Patent Specification Nos. 55,011,537, 56,015,272 and 56,092,857 also possess, in the form of 2,5-dihalogenobenzoyl(thio)urea derivatives, an insecticidal activity.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali out limed substrates (substrates coated with lime).

The active compounds according to the invention are also suitable for combating ectoparasites and endoparasites in the field of livestock husbandry and livestock breeding, and it is possible to achieve better results, for example higher milk outputs, higher weight, more attractive animal skin, longer lifespan, etcetera, by combating the pests.

The active compounds according to the invention are used in a known manner in these fields, such as by external application, for example in the form of dipping, spraying, pouring-on and spotting-on, and dusting, and by oral administration, for example via the feed or drinking water, for example in the form of tablets, capsules, drinks or granules.

The examples which follow illustrate the activity of the active compounds according to the invention.

EXAMPLE A

Plutella test

Solvent: 3 parts by weight of dimehylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*), as long as the leaves are still moist.

After the specified periods of time, the destruction in % is determined. 100% means that all the caterpillars have been killed; 0% means that none of the caterpillars have been killed. (Control)

In this test, for example, the compounds of Preparation Examples (4), (6), (7), (9), (14), (16), (24), (27), (30), (32), (33), (36), (38), (39), (40), (42), (47) and (50) showed a degree of destruction of 100% after 7 days, for example at a concentration of 0.001%.

EXAMPLE B

Laphygma test

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Laphygma frugiperda*), as long as the leaves are still moist.

After the specified periods of time, the destruction in % is determined. 100% means that all the caterpillars have been killed; 0% (control) means that none of the caterpillars have been killed.

In this test, for example, the compounds of Preparation Examples (1), (2) and (9) showed a degree of destruction of 100% after 7 days, for example at an active compound concentration of 0.001%.

The examples which follow are intended to illustrate the preparation of the compounds according to the invention:

EXAMPLE 1

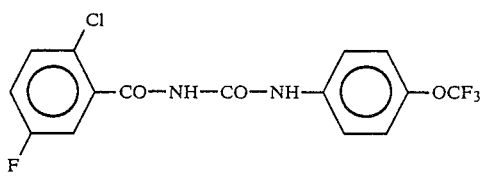

(Process variant a)

2.99 g (0.015 mol) of 2-chloro-5-fluoro-benzoyl isocyanate are added to 2.66 g (0.015 mol) of 4-trifluoromethoxyaniline in 30 ml of dry toluene, at 60° C., in the absence of moisture. The mixture is stirred for one hour at 80° C. and cooled to 20°–25° C. The precipitated product is filtered off under suction and dried in vacuo at 100° C. 5.6 g (100% of theory) of 1-(2-chloro-5-fluoro-benzoyl)-3-(4-trifluoromethoxyphenyl)-urea of melting point 199° C. are obtained.

(Process variant b)

A solution of 4.06 g (0.02 mol) of 4-trifluoromethoxyphenyl isocyanate in 10 ml of dry toluene is added to 3.48 g (0.02 mol) of 2-chloro-5-fluorobenzamide in 100 ml of dry toluene, at 100° C., in the absence of moisture. The mixture is boiled under reflux for 10 hours. After it has been cooled, the precipitated product is filtered off under suction and rinsed with methanol. 6.2 g (82.5% of theory) of 1-(2-chloro-5-fluoro-benzoyl)-3-(4-trifluoromethoxyphenyl)-urea of melting point 199° C. are obtained. The compound is identical to the compound prepared by process variant (a).

The compounds of the formula (Ia) which are listed in the table below can be prepared analogously to Example 1 and process variants (a) and (b):

TABLE 1

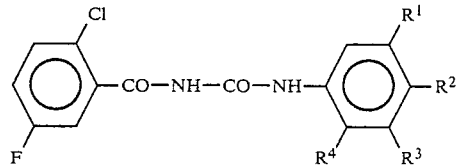

| Example No. | $R^1$ | $R^2$ | $R^3$ | $R^4$ | Melting point (°C.) |
|---|---|---|---|---|---|
| 2 | H | $CF_3$ | H | H | 225 |
| 3 | H | Cl | H | H | 206 |
| 4 | H | $SCF_3$ | H | H | 176 |
| 5 | H | tert.$C_4H_9$ | H | H | 193 |
| 6 | H | $COOC_4H_9$—tert. | H | H | 185 |
| 7 | Cl | $COOC_4H_9$—tert. | H | H | 207 |
| 8 | H | $OCHF_2$ | H | H | 175 |
| 9 | Cl | —O—C₆H₃(NO₂) | Cl | H | 212 |
| 10 | H | $O$—$CF_2$—$CHCl_2$ | H | H | 173 |
| 11 | Cl | Cl | H | H | 203 |
| 12 | H | Br | H | H | 200 |
| 13 | H | F | H | H | 184 |
| 14 | Cl | H | Cl | H | 169 |
| 15 | H | $NO_2$ | H | H | 226 |
| 16 | Cl | —O—C₆H₄—CN | Cl | H | 217 |
| 17 | $CF_3$ | H | $CF_3$ | H | 138 |
| 18 | —O—$CH_2$—$CF_2$—O— | | H | H | 183 |
| 19 | $CF_3$ | H | H | $CF_3$ | 114 |
| 20 | $CF_3$ | $CF_3$ | H | H | 164 |
| 21 | $CF_3$ | H | H | H | 166 |
| 22 | $CF_3$ | $OCH_3$ | H | H | 191 |
| 23 | $CF_3$ | Cl | H | H | 173 |
| 24 | Cl | —O—C₆H₃(Cl)(NO₂) | Cl | H | 213 |
| 25 | $CF_3$ | F | H | H | 159 |
| 26 | H | —O—C₆H₃(Cl)($CF_3$) | H | H | 156 |
| 27 | H | $SO_2CF_3$ | H | H | 202 |
| 28 | H | —O—C₆H₄—Cl | H | H | 187 |
| 29 | H | —O—C₆H₄—CN | Cl | H | 202 |
| 30 | H | —O—C₆H₃(Cl)(Cl) | Cl | H | 142 |
| 31 | Cl | —O—C₆H₄—$C(CH_3)_3$ | Cl | H | 190 |
| 32 | $CH_3$ | —O—C₆H₄—Cl | $CH_3$ | H | 177 |
| 33 | $CH_3$ | —O—C₆H₄—Cl | Cl | H | 180 |
| 34 | H | —O—C₆H₄—$CF_3$ | H | H | 172 |
| 35 | $CF_3$ | $SCH_3$ | H | H | 157 |
| 36 | Cl | $SCF_2Cl$ | H | H | 144 |
| 37 | Cl | $SCF_3$ | H | H | 173 |
| 38 | Cl | —$OCF_2$—$CHFCl$ | H | H | 168 |
| 39 | H | —$OCF_2$—$CHF$—$CF_3$ | H | H | 177 |
| 40 | H | $OCF_2Cl$ | H | H | 191 |
| 41 | $SCF_3$ | H | H | H | 137 |
| 42 | —O—$CFCl$—$CF_2$—O— | | H | H | 172 |
| 43 | Cl | —O—C₆H₄—$OSO_2CH_3$ | Cl | H | 197 |

TABLE 1-continued

Structure (Ia):

2-Cl, 5-F phenyl–CO—NH—CO—NH–phenyl(R¹, R², R³, R⁴)

| Example No. | R¹ | R² | R³ | R⁴ | Melting point/(°C.) |
|---|---|---|---|---|---|
| 44 | Cl | —O—(C₆H₄)—OCH₃ | Cl | H | 209 |
| 45 | H | H | H | OCF₃ | 125 |
| 46 | | —O—CF₂—O— | H | Cl | 206 |
| 47 | —O—CHF—CF₂—O— | | H | H | 194 |
| 48 | | —O—CF₂—O— | H | H | 189 |
| 49 | OCHF₂ | OCHF₂ | H | H | 177 |
| 50 | Cl | OCF₂—CHF₂ | H | H | 171 |
| 51 | Cl | —O—(C₆H₄)—OCH(CH₃)₂ | Cl | H | 146 |
| 52 | Cl | —O—(C₆H₂)(CH₃)₂—SCH₃ | Cl | H | 234 |
| 53 | Cl | —O—(C₆H₄)—OCF₃ | Cl | H | 187 |
| 54 | Cl | —CO—OCH₂CF₃ | H | H | 159 |
| 55 | Cl | —O—(C₆H₅) | Cl | H | 170 |
| 56 | H | —CO—OCH₂CF₃ | H | H | 175 |
| 57 | CF₃ | —OCHF₂ | H | H | 151 |
| 58 | H | —OCF₂CHFCl | H | H | 190 |
| 59 | H | —CF₃ | H | Cl | 203 |
| 60 | Cl | —O—(C₆H₄)—CH₂—S—C₂H₅ | Cl | H | 192 |
| 61 | Cl | —O—(C₆H₄)—OCH(CH₃)₂ | H | H | 132 |
| 62 | Cl | —O—(C₆H₃)(Cl)—OCF₃ | Cl | H | 169 |
| 63 | | —CF₂—O—CF₂—O | H | H | 184 |

The preparation of the starting compounds of the formula V can, for example, be carried out as follows:

1.8 liters of anhydrous hydrofluoric acid are initially introduced into a 5 liter stirred vessel with a cooler (−10° C.), 726 g of 2-chloro-5-amino-benzoic acid are then introduced in portions at −5° to 0° C., 480 g of NaNO₂ are then introduced, likewise in portions, at 0°–5° C., the mixture is stirred for a further 30 minutes and 800 ml of dimethylsulphoxide are then added. The reaction is allowed to continue at 80°–85° C. until splitting off of N₂ is complete. The mixture is cooled, and poured onto approx. 5 kg of ice, the precipitate is filtered off under suction, the residue from filtration is dissolved in an alkaline medium, the solution is filtered, the product is again precipitated with HCl, the precipitate is filtered off under suction, the residue from filtration is again dissolved in CH₂Cl₂ (in order to free it from residual NaF), and the solution is filtered and again concentrated.

Yield: 465 g m.p.: 145°–6° C.

350 g of the above acid are introduced into initially taken, excess thionyl chloride. After the addition and the HCl evolution are complete, the mixture is heated to approx. 100° C., and, after the reaction is complete, is worked up by distillation. Yield: 317 g boiling point 103° C./24 mbar $n_D^{20}$: 1.5487

By reaction with excess approx. 12.5% strength NH₃ solution, and after filtration, 258 g of 2-chloro-5-fluoro-benzamide are obtained m.p.: 138° C.

It will be appreciated that the instant specification and examples are set forth by way of illustration and not limitation, and that various modifications and changes may be made without departing from the spirit and scope of the present invention.

We claim:

1. A 2,5-dihalogenobenzoyl-(thio)urea of the formula

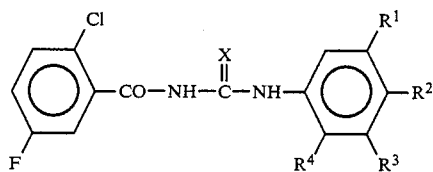

in which
X represents sulphur or oxygen,
R¹ represents hydrogen, halogen, or optionally substituted radicals from the series comprising alkyl, alkoxy and alkylthio,
R² represents hydrogen, halogen, cyano, nitro or optionally substituted radicals from the series comprising alkyl, alkylthio, alkylsulphonyl, alkoxy, aryloxy, alkylcarbonyl, alkoxycarbonyl, alkoxycarbonylalkyl and alkoxycarbonylalkylthio,
R¹ and R² together represent an optionally substituted alkylenedioxy radical or represent —CF₂—O—CF₂—O—,
R³ represents hydrogen, halogen, or an optionally substituted alkyl, alkoxy or aryloxy radical, and
R⁴ represents hydrogen, halogen, or optionally substituted radicals from the series comprising alkyl, alkylthio and alkoxy.

2. A compound according to claim 1, in which
R¹ represents hydrogen, halogen, or an optionally halogen-substituted radical from the series comprising C₁-C₆-alkyl, C₁-C₆-alkoxy and C₁-C₆-alkylthio,
R² represents hydrogen, cyano, nitro, halogen, or an optionally halogen-substituted radical from the series comprising C₁-C₆-alkyl, C₁-C₆-alkylthio, C₁-C₆-alkylsulphonyl, C₁-C₆-alkoxy, C₁-C₆-alkylcarbonyl, $C_1-C_6$-alkoxycarbonyl, $C_1-C_6$-alkoxycarbonylalkyl and $C_1-C_6$-alkoxycarbonylalkylthio, or represents a phenoxy which is optionally substituted by halogen, cyano, nitro, phenyl, trifluoromethyl, trifluoromethoxy, trifluoromethylthio, $C_1-C_6$-alkyl, $C_1-C_6$-alkoxy, $C_1-C_6$-alkylthio, $C_1-C_6$-alkylthioalkyl, $C_1-C_6$-alkylsulphonyloxy and/or $C_1-C_6$-alkoxycarbonyl, or $R^1$ and $R^2$ together represent alkylenedioxy which has 1 to 3 carbon atoms and is optionally substituted by fluorine and/or chlorine, or represent $-CF_2-O-CF_2-O-$, $R^3$ represents hydrogen, halogen, or an optionally halogen-substituted $C_1-C_6$-alkyl, $C_1-C_6$-alkoxy or phenoxy radical, and $R^4$ represents hydrogen, halogen, or optionally halogen-substituted radicals from the series comprising $C_1-C_6$-alkyl, $C_1-C_6$-alkylthio and $C_1-C_6$-alkoxy.

3. A compound according to claim 1, in which $R^1$ represents hydrogen, fluorine, chlorine or bromine, $R^2$ represents hydrogen, chlorine, bromine, fluorine, cyano, nitro, methyl, ethyl, n-propyl, i-propyl, n-butyl- i-butyl, sec.butyl, tert.butyl, trifluoromethyl, difluoromethyl, 1,1-difluoroethyl, 1,1,2,2,2-pentafluoroethyl, trifluoromethoxy, difluoromethoxy, chlorodifluoromethoxy, 2-chloro-1,1,2-trifluoroethoxy, 1,1,2,2-tetrafluoroethoxy, 2,2-dichloro-1,1-difluoroethoxy, 1,1,2,3,3,3-hexafluoropropoxy, trifluoromethylthio, difluoromethylthio, chlorodifluoromethylthio, 2-chloro-1,1,2-trifluoroethylthio, methoxycarbonyldifluoromethylthio, 1,1,2,3,3-hexafluoropropylthio, trifluoromethylsulphonyl or methoxy-, ethoxy-, n-propoxy-, i-propoxy-, n-butoxy-, i-butoxy-, sec-butoxy- or tert. butoxycarbonyl, or represents phenoxy which is optionally substituted by halogen, nitro, cyano, $C_1-C_6$-halogenoalkyl or $C_1-C_4$-alkoxycarbonyl, or $R^1$ and $R^2$ together represent difluoromethylenedioxy or represent $-CF_2-O-CF_2-O-$ or represent ethylenedioxy which is substituted by 3 or 4 fluorine atoms or by 3 fluorine atoms and 1 chlorine atom, $R^3$ represents hydrogen, fluorine, chlorine or bromine, and $R_4$ represents hydrogen, chlorine, bromine, trifluoromethyl, trifluoromethoxy or trifluoromethylthio.

4. A compound according to claim 1, in which

X represents oxygen, $R^1$ represents hydrogen or chlorine, $R^2$ represents hydrogen, trifluoromethyl, trifluoromethoxy, difluoromethoxy, chlorodifluoromethoxy, chlorotrifluoroethoxy, n-pentafluoropropoxy, trifluoromethylthio, chlorodifluoromethylthio, tert.butoxycarbonyl, 4-nitrophenoxy, 4-cyanophenoxy or 4-trifluoromethylphenoxy, 4-1,1,2,2-tetrafluorethoxy or $R^1$ and $R^2$ together represent chlorotrifluoroethylenedioxy or $-CF_2-O-CF_2-O-$, $R^3$ represents hydrogen or chlorine, and $R^4$ represents hydrogen.

5. A compound according to claim 1, wherein such compound is 1-(2-chloro-5-fluoro-benzoyl)-3-(4-trifluoromethoxy-phenyl)urea of the formula

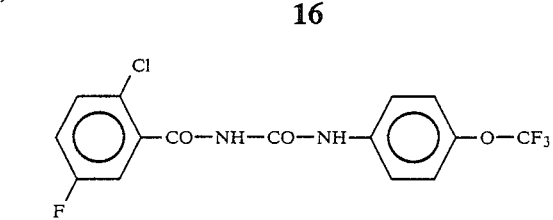

6. A compound according to claim 1, wherein such compound is 1-(2-chloro-5-fluorobenzoyl)-3-(4-tert.butoxycarbonylphenyl)urea of the formula

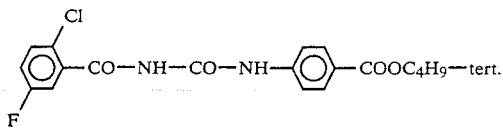

7. A compound according to claim 1, wherein such compound is 1-(2-chloro-5-fluorobenzoyl)-3-(3-chloro-4-(chlorodifluoromethylthiophenyl)-urea of the formula

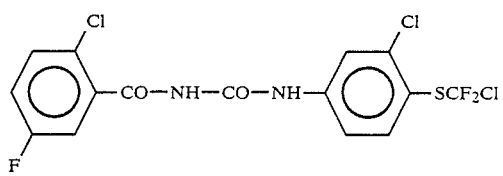

8. A compound according to claim 1, wherein such compound is 1-(2-chloro-5-fluorobenzoyl)-3-(4-chlorodifluoromethoxyphenyl)urea of the formula

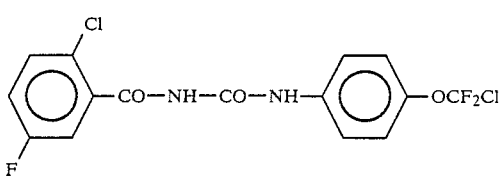

9. A compound according to claim 1, wherein such compound is 1-(2-chloro-5-fluorobenzoyl)-3-(3-chloro-4-(1,1,2,2-tetrafluoroethoxyphenyl)-urea of the formula

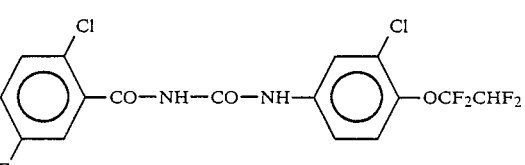

10. An insecticidal composition comprising an insecticidally effective amount of a compound according to claim 1 and a diluent.

11. A method of combating insects which comprises applying to such insects an insecticidally effective amount of a compound according to claim 1.

12. The method according to claim 11, wherein such compound is 1-(2-chloro-5-fluoro-benzoyl)-3-(4-trifluoromethoxyphenyl)-urea, 1-(2-chloro-5-fluorobenzoyl)-3-(4-tert.butoxycarbonylphenyl)urea, 1-(2-chloro-5-fluorobenzoyl)3-(3-chloro-4(chlorodifluoromethylthiophenyl)-urea, 1-(2-chloro-5-fluorobenzoyl)-3-(4-chlorodifluoromethoxyphenyl)-urea, or 1-(2-chloro-5-fluorobenzoyl)-3-(3-chloro-4-(1,1,2,2-tetrafluoroethoxyphenyl)-urea.

* * * * *